United States Patent [19]
Gers-Barlag et al.

[11] Patent Number: 5,833,960
[45] Date of Patent: Nov. 10, 1998

[54] FOAMING LIGHT PROTECTION PREPARATIONS CONTAINING WATER-SOLUBLE LIGHT PROTECTION FILTERS AND SURFACE-ACTIVE SUBSTANCES

[75] Inventors: Heinrich Gers-Barlag, Kummerfeld; Anja Müller; Peter Maurer, both of Hamburg, all of Germany

[73] Assignee: Beiersdorf AG, Hamburg, Germany

[21] Appl. No.: 902,377

[22] Filed: Jul. 29, 1997

[30] Foreign Application Priority Data

Aug. 2, 1996 [DE] Germany .............................. 196 31 221.3

[51] Int. Cl.$^6$ .............................. A61K 7/42; A61K 7/00; A61K 31/70; A61K 31/22
[52] U.S. Cl. .............................. 424/59; 424/60; 424/400; 424/401; 514/23; 514/25; 514/546
[58] Field of Search ................................ 424/59, 60, 400, 424/401; 514/557, 558, 23, 25, 546

[56] References Cited

U.S. PATENT DOCUMENTS

| | | | |
|---|---|---|---|
| 5,039,516 | 8/1991 | Goodman et al. | 424/59 |
| 5,605,486 | 2/1997 | McCook et al. | 424/59 |
| 5,656,280 | 8/1997 | Herb et al. | 424/401 |

*Primary Examiner*—Shelley A. Dodson
*Attorney, Agent, or Firm*—Sprung Kramer Schaefer & Briscoe

[57] ABSTRACT

Active substance combinations of
(a) one or more surface-active substances selected from the group comprising glucose derivatives,
(b) one or more surface-active substances selected from the group comprising glycerol monocarboxylic or dicarboxylic acid monoesters and
(c) one or more water-soluble, cosmetically or pharmaceutically acceptable UV filters.

19 Claims, No Drawings

FOAMING LIGHT PROTECTION PREPARATIONS CONTAINING WATER-SOLUBLE LIGHT PROTECTION FILTERS AND SURFACE-ACTIVE SUBSTANCES

The present invention relates to cosmetic and dermatological light protection preparations, especially cosmetic and dermatological light protection skin care preparations. In one particular embodiment the present invention further relates to after-foaming cosmetic and dermatological light protection preparations.

BACKGROUND OF THE INVENTION

The damaging effect of the ultraviolet part of solar radiation on the skin is generally known. Whereas rays with a wavelength of less than 290 nm (the so-called UVC region) are absorbed by the ozone layer in the earth's atmosphere, rays in the region between 290 nm and 320 nm, the so-called UVB region, cause erythema, simple sunburn or even burns of a greater or lesser degree.

The narrower region around 308 nm is given as a maximum for the erythematous activity of sunlight.

Numerous compounds are known for providing protection against UVB radiation, said compounds usually being derivatives of 3-benzylidenecamphor, 4-aminobenzoic acid, cinnamic acid, salicylic acid, benzophenone and also 2-phenylbenzimidazole.

It is also important to have filters for the region between about 320 nm and about 400 nm, the so-called UVA region, because its rays too can cause damage. Thus it is found that UVA radiation leads to damage of the elastic and collagenous fibres of the connective tissue, causing premature ageing of the skin, and that it is to be regarded as a cause of numerous phototoxic and photoallergic reactions. The damaging effect of UVB radiation can be reinforced by UVA radiation.

However, UV radiation can also lead to photochemical reactions, in which case the photochemical reaction products intervene in the skin's metabolism.

Such photochemical reaction products are predominantly free radical compounds, e.g. hydroxyl radicals. Undefined free radical photochemical products formed in the skin itself can also be responsible for uncontrolled consecutive reactions to daylight because of their high reactivity. However, singlet oxygen, a non-radical excited state of the oxygen molecule, can also occur under UV irradiation, as can short-lived epoxides and many other species. Singlet oxygen, for example, differs from the normal triplet oxygen (radical ground state) by its increased reactivity. However, excited reactive (radical) triplet states of the oxygen molecule also exist.

Furthermore, UV radiation is a type of ionizing radiation. Thus there is the risk that UV exposure may also create ionic species, which in turn are then capable of oxidative intervention in the biochemical processes.

2-Phenylbenzimidazole-5-sulphonic acid and its salts, especially the sodium, potassium and TEA salts, obtainable for example under the name Eusolex® 232 from Merck AG, which has the following structural formula:

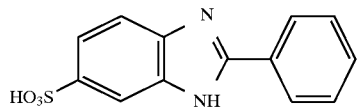

are water-soluble UV filters which are advantageous per se.

Another known and advantageous, albeit water-insoluble, light protection filter is 4-(tert-butyl)-4'-methoxydibenzoylmethane, which has the structure

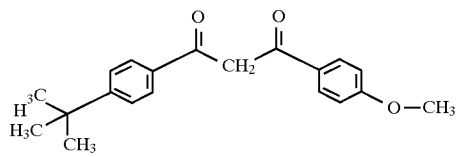

and is marketed by Givaudan under the trademark Parsol® 1789.

The main disadvantage of this substance is a degree of instability to UV radiation, so preparations containing this substance should also have certain UV stabilizers incorporated therein.

Another advantageous UVB filter is tris(2-ethyl-hexyl) 4,4',4"-(1,3,5-triazine-2,4,6-triyltriimino)tris-benzoate, synonymously called 2,4,6-tris[anilino(p-carbo-2'-ethyl-1'-hexyloxy)]-1,3,5-triazine:

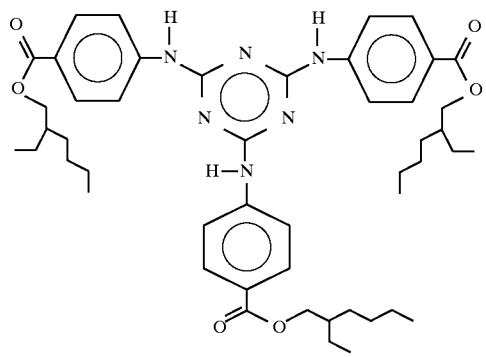

This UVB filter is marketed by BASF Aktiengesell-schaft under the trademark UVINUL® T 150 and is distinguished by good UV absorption properties.

The main disadvantage of this UVB filter is its poor solubility in lipids. Known solvents for this UVB filter can dissolve a maximum of ca. 15% by weight of this filter, corresponding to about 1–1.5% by weight of dissolved, i.e. active, UV filter.

Another advantageous light protection filter is 4-methylbenzylidenecamphor, which has the structure

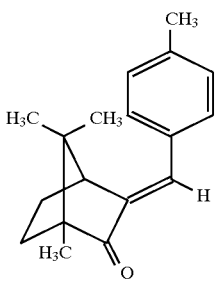

and is marketed by Merck under the trademark Eusolex® 6300. These substances are distinguished per se by good UV filter properties. Their use concentration is limited, however, when they are in combination with one another or with other substances present as solids.

Another advantageous light protection filter is 2-ethylhexyl p-methoxycinnamate, which is obtainable from Givaudan under the trademark Parsol® MCX and has the following structure:

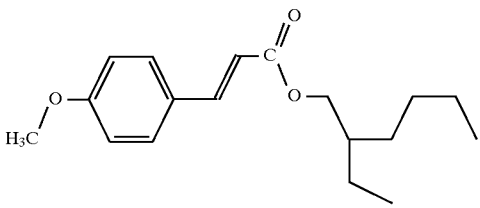

Yet another advantageous light protection filter is ethylhexyl 2-cyano-3,3-diphenylacrylate (octocrylene), which is obtainable from BASF under the trademark UVINUL® N 539 and has the following structure:

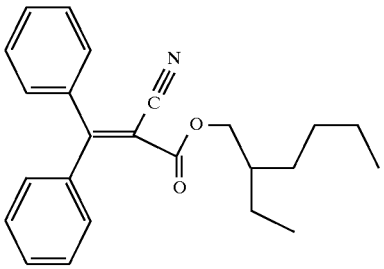

Especially when several light protection substances which are crystalline under normal conditions are present, said light protection substances being selected for example from the group comprising tris(2-ethylhexyl) 4,4',4"-(1,3,5-triazine-2,4,6-triyl-triimino)trisbenzoate, 4-methylbenzylidenecamphor and 4-(tert-butyl)-4'-methoxydibenzoylmethane, and especially when titanium dioxide is additionally present as an insoluble component, only low use concentrations and hence low light protection factors are possible according to the teachings of the state of the art; the amount of oil phase would otherwise be disproportionately increased, which would also have disadvantages.

UV absorbers or UV reflectors are mostly inorganic pigments, which are used in known manner in cosmetics for protecting the skin from UV rays. Said inorganic pigments are oxides of titanium, zinc, iron, zirconium, silicon, manganese, aluminium and cerium and mixtures thereof, as well as modifications.

Inorganic pigments are distinguished per se by a good light protection effect. However, they have the disadvantage of being difficult to incorporate satisfactorily into such formulations. Only when the particles in the final formulation are very small are they not observed to produce a disturbing "whitening" (formation of white spots) after application to the skin. The particle sizes of such pigments are usually in the range below 100 nm. In a conventional emulsion the particles have a greater or lesser tendency to form agglomerates which are visible even under the light microscope. Moreover, such agglomeration does not end with the process for the manufacture of a particular preparation, but continues during storage. The "whitening" can therefore increase over a prolonged period of time. In the medium or long term, this type of agglomeration can also cause an emulsion to lose oil phase or even break.

A further disadvantage of using inorganic pigments in cosmetic formulations is that such pigments lead to severe dryness of the skin in the vast majority of cases.

Nevertheless, the disadvantage of the state of the art was that normally either only comparatively low light protection factors could be achieved, or that the light protection filters had an insufficient UV stability, an insufficient physiological compatibility or an insufficiently high solubility or dispersibility in cosmetic or dermatological preparations, or exhibited other incompatibilities with cosmetic or dermatological preparations, or had several disadvantages simultaneously.

Foaming cosmetic preparations are known per se. Foams allow a fine distribution of active substances on the skin. However, foams are normally only obtainable by using special surfactants whose compatibility with the skin is often poor.

After-foaming preparations are often found as special products such as after-foaming shaving gels or the like. These products are initially applied to the skin in fluid form from an aerosol container and only then, after a short wait, develop the actual foam under the influence of the after-foaming agent present. The advantage of such preparations compared with ready-made foams, for example, which are already in the form of a foam when applied to the skin from the aerosol container, is improved wetting.

Thus after-foaming preparations are known per se. U.S. Pat. No. 3,541,581 names water, soap (i.e. water-soluble salts of higher fatty acids), gelling agents and after-foaming agents as essential constituents of such a preparation. Other preparations of this type are also known, but they all have the disadvantage of being cosmetically inelegant and/or failing to meet the requirement of a low irritation potential. Apart from these, specially after-foaming light protection preparations have hitherto been totally unknown to the state of the art, the known state of the art consisting essentially of after-foaming shaving preparations and possibly some marginal products.

One object of the present invention was to enrich the state of the art in this direction.

Another object of the present invention was thus to remedy at least some if not all of these disadvantages.

SUMMARY OF THE INVENTION

It was surprising, and could not be anticipated by those skilled in the art, that active substance combinations of (a) one or more surface-active substances selected from the group comprising glucose derivatives of the structural formula

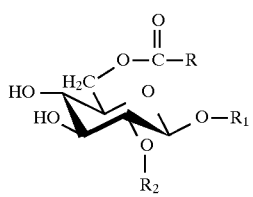

in which R is a branched or unbranched alkyl radical having 1 to 24 carbon atoms, $R_1$ is either a hydrogen atom or a branched or unbranched alkyl radical having 1 to 24 carbon atoms and $R_2$ is either a hydrogen atom or a branched or unbranched acyl radical having 1 to 24 carbon atoms, (b) one or more surface-active substances selected from the group comprising glycerol monocarboxylic or dicarboxylic acid monoesters of the general formula

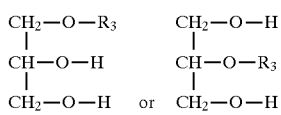

in which $R_3$ is a branched or unbranched acyl radical having 6–24 carbon atoms, and (c) one or more water-soluble, cosmetically or pharmaceutically acceptable UW filters remedy the disadvantages of the state of the art.

DETAILED DESCRIPTION OF THE INVENTION

In particular, the present invention is embodied by cosmetic or pharmaceutical preparations which contain active substance combinations of (a) one or more surface-active substances selected from the group comprising glucose derivatives of the structural formula

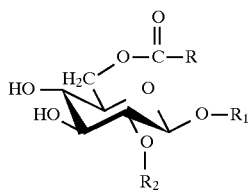

in which R is a branched or unbranched alkyl radical having 1 to 24 carbon atoms, $R_1$ is either a hydrogen atom or a branched or unbranched alkyl radical having 1 to 24 carbon atoms and $R_2$ is either a hydrogen atom or a branched or unbranched acyl radical having 1 to 24 carbon atoms, (b) one or more surface-active substances selected from the group comprising glycerol monocarboxylic or dicarboxylic acid monoesters of the general formula

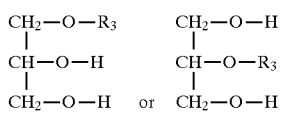

in which $R_3$ is a branched or unbranched acyl radical having 6–24 carbon atoms, (c) one or more water-soluble, cosmetically or pharmaceutically acceptable UV filters, (d) an aqueous phase which may contain conventional, substances soluble and/or dispersible therein, including especially other cosmetically or pharmaceutically acceptable UV filters, and (e) optionally an oil phase which may contain conventional substances soluble and/or dispersible therein, including especially other cosmetically or pharmaceutically acceptable UV filters and are in the form of foams.

In particular, the use of active substance combinations of (a) one or more surface-active substances selected from the group comprising glucose derivatives of the structural formula

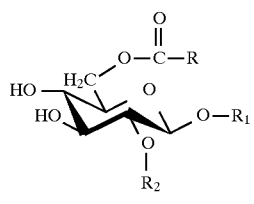

in which R is a branched or unbranched alkyl radical having 1 to 24 carbon atoms, $R_1$ is either a hydrogen atom or a branched or unbranched alkyl radical having 1 to 24 carbon atoms and $R_2$ is either a hydrogen atom or a branched or unbranched acyl radical having 1 to 24 carbon atoms, (b) one or more surface-active substances selected from the group comprising glycerol monocarboxylic or dicarboxylic acid monoesters of the general formula

```
CH2—O—R3        CH2—O—H
 |               |
CH—O—H          CH—O—R3
 |               |
CH2—O—H   or   CH2—O—H
``` in which $R_3$ is a branched or unbranched acyl radical having 6–24 carbon atoms, (c) one or more water-soluble, cosmetically or pharmaceutically acceptable UV filters, (d) an aqueous phase which may contain conventional substances soluble and/or dispersible therein, including especially other cosmetically or pharmaceutically acceptable UW filters, and (e) optionally an oil phase which may contain conventional substances soluble and/or dispersible therein, including especially other cosmetically or pharmaceutically acceptable UV filters for the production of cosmetic or pharmaceutical preparations in the form of foams represents an advantageous embodiment of the present invention.

R is advantageously selected from the group comprising unbranched alkyl radicals, the myristyl radical, the palmityl radical, the stearyl radical and the eicosyl radical being preferred.

$R_1$ can advantageously be a hydrogen atom but is preferably selected from the group comprising methyl, ethyl, propyl and isopropyl.

$R_2$ can advantageously be a hydrogen atom but can equally advantageously be selected from the group comprising myristoyl, palmitoyl, stearoyl and eicosoyl.

Methyl glucose sesquistearate, which consists of roughly equal parts of the substances

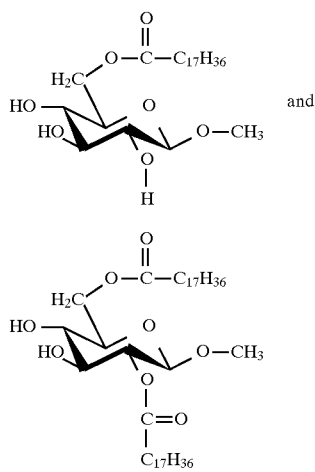

is particularly advantageously chosen as the surface-active substance from the group comprising glucose derivatives. Such mixtures are commercially available, for example under the trademark Tego® Care PS from Th. Goldschmidt KG.

$R_3$ is preferably a myristyl radical, palmityl radical, stearyl radical or eicosyl radical.

Glyceryl stearate, which is commercially available, for example under the trademark Tegin® M from Th. Goldschmidt KG, has proved particularly advantageous, in terms of the present invention, as a surface-active substance listed under item (b).

Advantageous water-soluble UV filters in terms of the present invention are especially those which carry one or more sulphonic acid groups or sulphonate groups on their molecular backbone. The following are particularly preferred:

2-Phenylbenzimidazole-5-sulphonic acid and its salts, for example the sodium or potassium salt or its triethanolammonium salt:

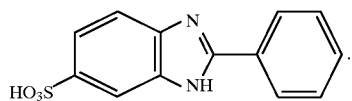

Sulphonic acid derivatives of benzophenones, preferably 2-hydroxy-4-methoxybenzophenone-5-sulphonic acid and its salts, for example the corresponding sodium, potassium or triethanolammonium salt:

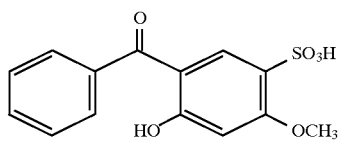

Sulphonic acid derivatives of 3-benzylidenecamphor, e.g. 4-(2-oxo-3-bornylidenemethyl) benzenesulphonic acid and its salts, for example the corresponding sodium, potassium or triethanolammonium salt:

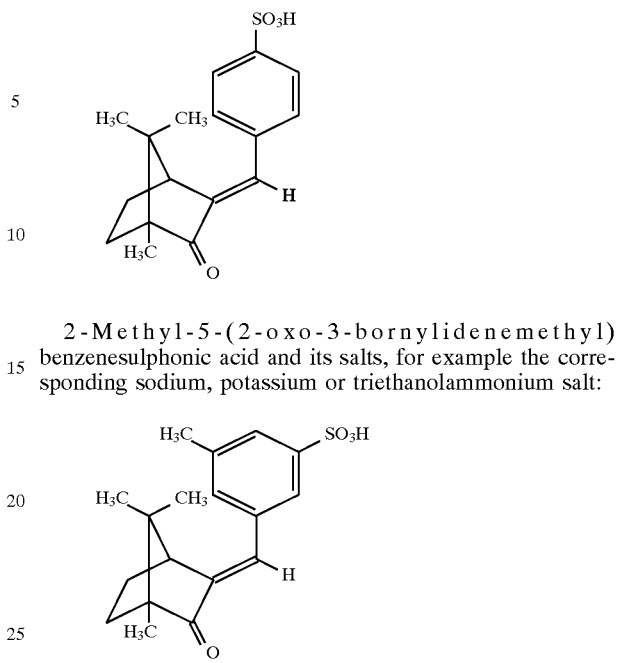

2-Methyl-5-(2-oxo-3-bornylidenemethyl) benzenesulphonic acid and its salts, for example the corresponding sodium, potassium or triethanolammonium salt:

1,4-Di(2-oxo-10-sulpho-3-bornylidenemethyl)benzene and its salts (the corresponding 10-sulphato compounds, for example the corresponding sodium, potassium or triethanolammonium salt), also called benzene-1,4-di(2-oxo-3-bornylidenemethyl-10-sulphonic acid):

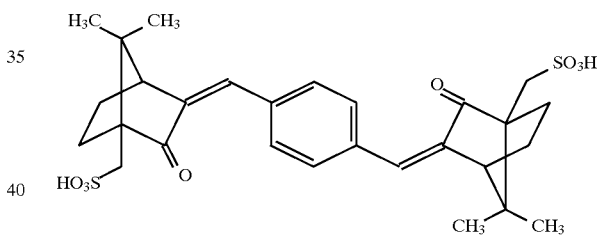

Phenylene-1,4-bis(2-benzimidazyl)-3,3', 5,5'-tetrasulphonic acid:

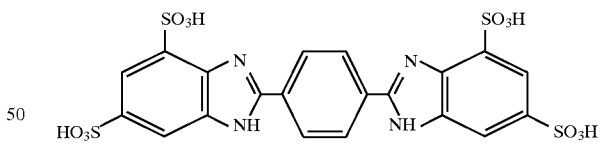

and its salts, for example the corresponding sodium, potassium or triethanolammonium salt, especially disodium phenylene-1,4-bis-(2-benzimidazyl)-3,3',5,5'-tetrasulphonate:

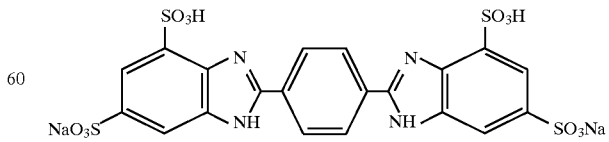

When unfoamed, i.e. immediately after the individual components have been brought together, compositions according to the invention are two-phase systems, normally emulsions. They can be foamed simply by gentle rubbing, for example in the hands, or by application to the skin and then rubbing, but also by stirring or other foaming processes.

Small-cell concentrated foams of outstanding cosmetic elegance are obtainable according to the invention. Such foams preferably represent light protection preparations which surprisingly remedy the described disadvantages of the state of the art. The light protection factors achievable according to the invention are higher than could have been anticipated from the state of the art.

Furthermore, in the cosmetic or dermatological preparations according to the invention, the less readily soluble components also have a better solubility than in the preparations of the state of the art, even when several such components are present.

According to the invention, the agglomeration of any inorganic pigment particles present (which are naturally in disperse and not dissolved form), with the consequences of "whitening", oil loss or breakage of the emulsion, can also be prevented, even when one or more less readily soluble components are additionally present.

The invention also provides light protection preparations which have a higher stability, especially stability to decomposition under the influence of light, very particularly UV light, than could have been anticipated from the state of the art. In particular, the stability of 4-(tert-butyl)-4'-methoxydibenzoyl-methane is drastically increased.

The invention also provides preparations of particularly good skin compatibility, making it possible to spread valuable ingredients particularly well on the skin.

According to the invention, the amounts of tris-(2-ethylhexyl) 4,4',4"-(1,3,5-triazine-2,4,6-triyltriimino) trisbenzoate, and also of the other light protection filters present as solids under normal conditions, used in cosmetic or dermatological preparations can be substantially increased compared with the state of the art.

On the other hand, the present invention makes it possible, with a smaller total concentration of UV filters, to achieve a comparable or even greater light protection filter effect than the state of the art allowed. For this purpose it has proved particularly advantageous to introduce an additional content of cosmetically or pharmaceutically acceptable electrolytes.

It was further surprising that, according to the invention, solutions of tris(2-ethylhexyl) 4,4', 4"-(1,3,5-triazine-2,4,6-triyltriimino)trisbenzoate are stabilized, since the latter substance not only has a poor solubility but also readily crystallizes out again from its solution.

The total amount of water-soluble UV filter or filters in the finished cosmetic or dermatological preparations is advantageously chosen within the range 0.1–10.0% by weight, preferably 0.5–6.0% by weight, based on the total weight of the preparations.

The total amount of 2-phenylbenzimidazole-5-sulphonic acid (if it is this substance which is to be used as a water-soluble UV filter in terms of the present invention) or its salts in the finished cosmetic or dermatological preparations is advantageously chosen within the range 0.1–10.0% by weight, preferably 0.5–6.0% by weight, based on the total weight of the preparations.

The total amount of 2-hydroxy-4-methoxy-benzophenone-5-sulphonic acid (if it is this substance which is to be used as a water-soluble UV filter in terms of the present invention) or its salts in the finished cosmetic or dermatological preparations is advantageously chosen within the range 0.1–10.0% by weight, preferably 0.5–6.0% by weight, based on the total weight of the preparations.

The total amount of 4-(2-oxo-3-bornylidene-methyl) benzenesulphonic acid (if it is this substance which is to be used as a water-soluble UV filter in terms of the present invention) or its salts in the finished cosmetic or dermatological preparations is advantageously chosen within the range 0.1–15% by weight, preferably 0.5–10% by weight, based on the total weight of the preparations.

The total amount of 2-methyl-5-(2-oxo-3-bornylidenemethyl)benzenesulphonic acid (if it is this substance which is to be used as a water-soluble UV filter in terms of the present invention) or its salts in the finished cosmetic or dermatological preparations is advantageously chosen within the range 0.1–10.0% by weight, preferably 0.5–6.0% by weight, based on the total weight of the preparations.

The total amount of benzene-1,4-di(2-oxo-3-bornylidenemethyl-10-sulphonic acid) (if it is this substance which is to be used as a water-soluble UV filter in terms of the present invention) or its salts in the finished cosmetic or dermatological preparations is advantageously chosen within the range 0.1–5.0% by weight, preferably 0.5–10.0% by weight, based on the total weight of the preparations.

The total amount of phenylene-1,4-bis(2-benzimidazyl)-3,3', 5,5'-tetrasulphonic acid (if it is this substance which is to be used as a sulphonated UV filter in terms of the present invention) or its salts in the finished cosmetic or dermatological preparations is advantageously chosen within the range 0.1–10.0% by weight, preferably 0.5–6.0% by weight, based on the total weight of the preparations.

The total amount of tris(2-ethylhexyl) 4,4',4"-(1,3,5-triazine-2,4,6-triyltriimino)trisbenzoate (as an additional UV filter optionally to be used per se) in the finished cosmetic or dermatological preparations is advantageously chosen within the range 0.1–10.0% by weight, preferably 0.5–6.0% by weight, based on the total weight of the preparations.

The total amount of 4-methylbenzylidenecamphor (as an additional UV filter optionally to be used per se) in the finished cosmetic or dermatological preparations is advantageously chosen within the range 0.1–10.0% by weight, preferably 0.5–6.0% by weight, based on the total weight of the preparations.

The total amount of 2-ethylhexyl p-methoxycinnamate (as an additional UV filter optionally to be used per se) in the finished cosmetic or dermatological preparations is advantageously chosen within the range 0.1–15% by weight, preferably 0.5–7.5% by weight, based on the total weight of the preparations.

The total amount of ethylhexyl 2-cyano-3,3-diphenylacrylate (as an additional UV filter optionally to be used per se) in the finished cosmetic or dermatological preparations is advantageously chosen within the range 0.1–15.0% by weight, preferably 0.5–10.0% by weight, based on the total weight of the preparations.

The total amount of 4-(tert-butyl)-4'-methoxydibenzoylmethane (as an additional UV filter optionally to be used per se) in the finished cosmetic or dermatological preparations is advantageously chosen within the range 0.1–10.0% by weight, preferably 0.5–6.0% by weight, based on the total weight of the preparations.

It is also advantageous to combine the active substance combinations according to the invention with other UVA and/or UVB filters.

Furthermore, it may also be advantageous to combine the active substance combinations according to the invention with other UVA and/or UVB filters, for example specific salicylic acid derivatives such as

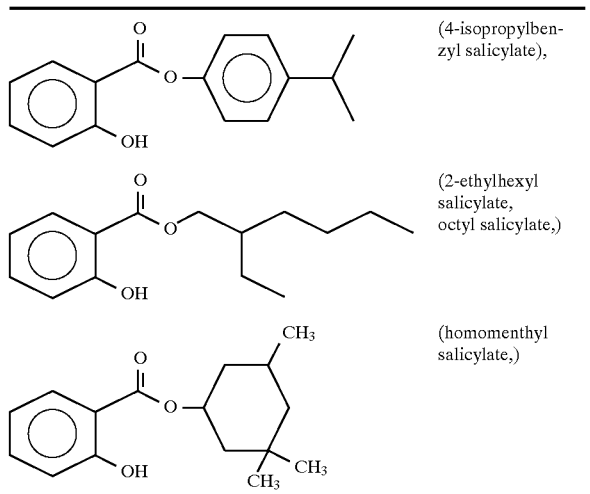

(4-isopropylbenzyl salicylate), (2-ethylhexyl salicylate, octyl salicylate,)

(homomenthyl salicylate,)

The total amount of one or more salicylic acid derivatives in the finished cosmetic or dermatological preparations is advantageously chosen within the range 0.1–15.0% by weight, preferably 0.5–8.0% by weight, based on the total weight of the preparations. If ethylhexyl salicylate is selected, its total amount is advantageously chosen within the range 0.1–5.0% by weight, preferably 0.5–2.5% by weight. If homomenthyl salicylate is selected, its total amount is advantageously chosen within the range 0.1–10.0% by weight, preferably 0.5–5.0 by weight.

It can also be advantageous to combine the combinations according to the invention with UVA filters which have hitherto conventionally been present in cosmetic preparations. These substances are preferably dibenzoylmethane derivatives, especially 1-(4'-tert-butylphenyl)-3-(4'-methoxyphenyl)propane-1,3-dione and 1-phenyl-3-(4'-isopropylphenyl)propane-1,3-dione. The invention also provides these combinations or preparations containing these combinations. The amounts can be those used for the UVB combination.

It is advantageous according to the invention to use other UVA filters and/or UVB filters in addition to the combinations according to the invention, the total amount of filters being e.g. 0.1% by weight to 30% by weight, preferably 0.5 to 10% by weight, based on the total weight of the preparations, in order to provide cosmetic preparations which protect the skin from the whole range of ultraviolet radiation. They can also be used as sunscreens.

Examples of advantageous oil-soluble UVB filters are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino)benzoate;

cinnamic acid esters, preferably 2-ethylhexyl 4-methoxycinnamate, isopentyl 4-methoxycinnamate;

benzophenone derivatives, preferably 2-hydroxy-4-methoxybenzophenone, 2-hydroxy-4-methoxy-4'-methylbenzophenone, 2,2'-dihydroxy-4-methoxybenzophenone;

benzalmalonic acid esters, preferably di-(2-ethylhexyl) 4-methoxybenzalmalonate;

2,4,6-trianilino(p-carbo-2'-ethyl-1'-hexyloxy)-1,3,5-triazine.

Of course, the list of said UVB filters which can be used in combination with the active substance combinations according to the invention is not intended to imply a limitation.

It is advantageous, but not compulsory, for cosmetic and dermatological preparations according to the invention also to contain inorganic pigments based on metal oxides and/or other metal compounds sparingly soluble or insoluble in water, especially the oxides of titanium ($TiO_2$), zinc (ZnO), iron (e.g. $Fe_2O_3$), zirconium ($ZrO_2$), silicon ($SiO_2$), manganese (e.g. MnO), aluminium ($Al_2O_3$) and cerium (e.g. $Ce_2O_3$), mixed oxides of said metals and mixtures of such oxides. Pigments based on $TiO_2$ are particularly preferred.

The inorganic pigments are preferably present in hydrophobic form, i.e. they are surface-treated to repel water. This surface treatment can consist in providing the pigments with a thin hydrophobic layer by processes known per se.

One such process consists for example in producing the hydrophobic surface layer according to the following reaction:

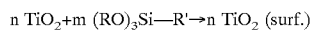

n and m being arbitrary stoichiometric parameters and R and R' being the desired organic radicals. Pigments rendered hydrophobic analogously to DE-OS 33 14 742, for example, are advantageous.

Advantageous $TiO_2$ pigments are obtainable for example under the tradenames T 805 from Degussa, MT 100 T from Tayca or M 160 from Kemira.

Products which can be chosen as water-dispersible inorganic micropigments are for example those obtainable under the trademark Tioveil® from Tioxide.

The total amount of inorganic pigments, especially hydrophobic inorganic micropigments (as additional substances optionally to be used per se), in the finished cosmetic or dermatological preparations is advantageously chosen within the range 0.1–30% by weight, preferably 0.1–10.0% by weight and especially 0.5–6.0% by weight, based on the total weight of the preparations.

The cosmetic and/or dermatological light protection formulations according to the invention can have the conventional compositions and can be used for cosmetic and/or dermatological protection from the light and also for the treatment, care and cleansing of the skin and/or hair, and as cosmetic make-up products.

For use, the cosmetic and dermatological preparations according to the invention are applied to the skin and/or hair in sufficient amount and in the manner conventional for cosmetics.

Particularly preferred cosmetic and dermatological preparations are those which are in the form of a sunscreen. Advantageously these can additionally contain at least one other UVA filter and/or at least one other UVB filter and/or at least one inorganic pigment, preferably an inorganic micropigment.

Another advantageous embodiment of the present invention consists of after-sun products, especially in the form of soothing foams with a cooling effect.

The cosmetic and dermatological preparations according to the invention can contain cosmetic auxiliaries such as those conventionally used in such preparations, e.g. preservatives, bactericides, perfumes, dyes, pigments with a colouring effect, thickeners, moisturizing and/or moisture-retaining substances, fats, oils, waxes or other conventional constituents of a cosmetic or dermatological formulation, such as alcohols, polyols, polymers, foam stabilizers, electrolytes, organic solvents or silicone derivatives.

As mentioned previously, the present invention makes it possible, with a smaller total concentration of UV filters, to achieve a comparable or even greater light protection filter effect than has hitherto been allowed by the state of the art. F this purpose it has proved particularly advantageous to introduce an additional content of cosmetically or pharmaceutically acceptable electrolytes. Over wide concentration ranges it is possible to reduce the concentration of the UV filter or filters by an amount which is the same as or at least comparable to that with which the formulation is made up, as it were, with one or more electrolytes. The lower limit at which this behaviour becomes noticeable in a manner relevant to the user has normally been found to be a total content of about 0.5% by weight of water-soluble UV filters.

The preparations according to the invention therefore preferably contain electrolytes, especially one or more salts with the following anions: chlorides and also inorganic oxo anions, including especially sulphates, carbonates, phosphates, borates and aluminates. Electrolytes based on organic anions can also advantageously be used, examples being lactates, acetates, benzoates, propionates, tartrates, citrates, amino acids and their salts, etc. Comparable effects can also be achieved by ethylenediaminetetraacetic acid and its salts.

Ammonium, alkylammonium, alkali metal, alkaline earth metal, magnesium, iron or zinc ions are preferably used as the cations of the salts. It is self-evident that only biocompatible electrolytes should be used in cosmetics. Potassium chloride, sodium chloride, magnesium sulphate, zinc sulphate and mixtures thereof are particularly preferred. Salt mixtures such as those occurring in the natural salt from the Dead Sea are also advantageous.

The concentration of the electrolyte or electrolytes should be about 0.1–10.0 by weight, particularly advantageously about 0.3–8.0% by weight, based on the total weight of the preparation.

An additional content of antioxidants is generally preferred. According to the invention, favourable antioxidants which can be used are any antioxidants suitable or conventional for cosmetic and/or dermatological applications.

The antioxidants are advantageously selected from the group comprising amino acids (e.g. glycine, histidine, tyrosine, tryptophan) and their derivatives, imidazoles (e.g. urocanic acid) and their derivatives, peptides such as D,L-carnosine, D-carnosine, L-carnosine and their derivatives (e.g. anserine), carotenoids, carotenes (e.g. $\alpha$-carotene, $\beta$-carotene, lycopene) and their derivatives, chlorogenic acid and its derivatives, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl, lauryl, palmitoyl, oleyl, $\gamma$-linoleyl, cholesteryl and glyceryl esters) and their salts, dilauryl thiodipropionate, distearyl thiodipropionate, thiodipropionic acid and its derivatives (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximine) in very low tolerated doses (e.g. pmol to $\mu$mol/kg), and also (metal) chelating agents (e.g. $\alpha$-hydroxy fatty acids, palmitic acid, phytic acid, lactoferrin), $\alpha$-hydroxy acids (e.g. citric acid, lactic acid, malic acid), humic acid, bile acid, bile extracts, bilirubin, biliverdin, EDTA, EGTA and its derivatives, unsaturated fatty acids and their derivatives (e.g. $\gamma$-linolenic acid, linoleic acid, oleic acid), folic acid and its derivatives, ubiquinone and ubiquinol and their derivatives, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin, rutic acid and its derivatives, $\alpha$-glycosylrutin, ferulic acid, furfurylideneglucitol, carnosine, butylhydroxytoluene, butylhydroxyanisole, nordihydroguaiac acid, nordihydroguaiaretic acid, trihydroxybutyrophenone, uric acid and its derivatives, mannose and its derivatives, zinc and its derivatives (e.g. ZnO, $ZnSO_4$), selenium and its derivatives (e.g. selenomethionine), stilbenes and their derivatives (e.g. stilbene oxide, trans-stilbene oxide), and the derivatives (salts, esters, ethers, sugars, nucleotides, nucleosides, peptides and lipids) of said active substances which are suitable according to the invention.

The amount of the abovementioned antioxidants (one or more compounds) in the preparations is preferably 0.001 to 30% by weight, particularly preferably 0.05–20% by weight and especially 1–10% by weight, based on the total weight of the preparation.

If the antioxidant or antioxidants are vitamin E and/or its derivatives, their respective concentrations are advantageously chosen within the range 0.001–10% by weight, based on the total weight of the formulation.

If the antioxidant or antioxidants are vitamin A or vitamin A derivatives or carotenes or their derivatives, their respective concentrations are advantageously chosen within the range 0.001–10% by weight, based on the total weight of the formulation.

The oil phase of the preparations according to the invention is advantageously selected from the group comprising esters of saturated and/or unsaturated, branched and/or unbranched alkanecarboxylic acids with a chain length of 3 to 30 C atoms and saturated and/or unsaturated, branched and/or unbranched alcohols with a chain length of 3 to 30 C atoms, and from the group comprising esters of aromatic carboxylic acids and saturated and/or unsaturated, branched and/or unbranched alcohols with a chain length of 3 to 30 C atoms. Such ester oils can then advantageously be selected from the group comprising isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semisynthetic and natural mixtures of such esters, e.g. jojoba oil.

The oil phase can also advantageously be selected from the group comprising branched and unbranched hydrocarbons and hydrocarbon waxes, silicone oils and dialkyl ethers, from the group comprising saturated or unsaturated, branched or unbranched alcohols, and from fatty acid triglycerides, namely the triglycerol esters of saturated and/or unsaturated, branched and/or unbranched alkanecarboxylic acids with a chain length of 8 to 24 C atoms, especially 12–18 C atoms. The fatty acid triglycerides can advantageously be selected for example from the group comprising synthetic, semi-synthetic and natural oils, e.g. olive oil, sunflower oil, soya oil, groundnut oil, rapeseed oil, almond oil, palm oil, coconut oil, palm kernel oil, etc.

Arbitrary mixtures of such oil and wax components can also advantageously be used in terms of the present invention.

The oil phase is advantageously selected from the group comprising 2-ethylhexyl isostearate, octyl-dodecanol, isotridecyl isononanoate, isoeicosane, 2-ethylhexyl cocoate, $C_{12-15}$-alkyl benzoate, caprylic/capric triglyceride and dicaprylyl ether.

Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous.

Of the hydrocarbons, paraffin oil, squalane and squalene can advantageously be used in terms of the present invention.

The oil phase can advantageously also contain cyclic or linear silicone oils or can consist entirely of such oils, although it is preferable for the oil phase to contain other oil phase components in addition to the silicone oil or silicone oils.

The silicone oil to be used according to the invention is advantageously cyclomethicone (octamethylcyclotetrasiloxane). However, the use of other silicone oils, for example hexamethylcyclotrisiloxane, polydimethylsiloxane and poly(methylphenylsiloxane), is also advantageous in terms of the present invention.

Mixtures of cyclomethicone and isotridecyl isononanoate and mixtures of cyclomethicone and 2-ethylhexyl isostearate are also particularly advantageous.

The oil phase content is advantageously between 1 and 50% by weight, preferably 2.5–30% by weight and particularly preferably 5–15% by weight, based on the total weight of the preparations.

The aqueous phase of the preparations according to the invention may advantageously contain alcohols, diols or polyols with a small number of C atoms, and their ethers, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols with a small number of C atoms, e.g. ethanol, isopropanol, propane-1,2-diol and glycerol, and especially one or more thickeners which can advantageously be selected from the group comprising silicon dioxide, aluminium silicates and polysaccharides or their derivatives, e.g. hyaluronic acid, xanthan gum and hydroxypropyl methyl cellulose, and particularly advantageously from the group comprising polyacrylates, preferably a polyacrylate from the group comprising the so-called Carbopols, for example Carbopols of types 980, 981, 1382, 2984 and 5984, in each case individually or in combination.

The following Examples will illustrate the present invention without implying a limitation. Unless indicated otherwise, all amounts, proportions and percentages are based on the weight and the total amount or on the total weight of the preparations.

EXAMPLE 1

|  | % by weight |
|---|---|
| Glyceryl stearate | 2.00 |
| Methyl glucose sesquistearate | 5.00 |
| Caprylic/capric triglyceride | 5.00 |
| Octyldodecanol | 5.00 |
| Dicaprylyl ether | 2.00 |
| Phenylbenzimidazolesulphonic acid | 4.00 |
| Glycerol | 3.00 |
| Tocopheryl acetate | 1.00 |
| NaOH | q.s. |
| Perfume, preservative | q.s. |
| Water | ad 100.00 |

EXAMPLE 2

|  | % by weight |
|---|---|
| Glyceryl stearate | 2.00 |
| Methyl glucose sesquistearate | 5.00 |
| Caprylic/capric triglyceride | 1.67 |
| Octyldodecanol | 1.67 |
| Dicaprylyl ether | 1.67 |
| Phenylbenzimidazolesulphonic acid | 4.00 |
| Butylene glycol | 3.00 |
| Tocopheryl acetate | 1.00 |
| NaOH | q.s. |
| Perfume, preservative | q.s. |
| Water | ad 100.00 |

EXAMPLE 3

|  | % by weight |
|---|---|
| Propellant (butane/isobutane/propane) | 5.00 |
| Glyceryl stearate | 2.00 |
| Methyl glucose sesquistearate | 5.00 |
| Caprylic/capric triglyceride | 1.67 |
| Octyldodecanol | 1.67 |
| Dicaprylyl ether | 1.67 |
| Phenylbenzimidazolesulphanic acid | 4.00 |
| Butylene glycol | 3.00 |
| Tocopheryl acetate | 1.00 |
| NaOH | q.s. |
| Perfume, preservative | q.s. |
| Water | ad 100.00 |

EXAMPLE 4

|  | % by weight |
|---|---|
| Glyceryl stearate | 2.00 |
| Methyl glucose sesquistearate | 5.00 |
| Caprylic/capric triglyceride | 5.00 |
| Octyldodecanol | 5.00 |
| Dicaprylyl ether | 1.67 |
| Benzene-1,4-di(2-oxo-3-bornylidene-methyl-10-sulphonic acid) | 4.00 |
| Glycerol | 3.00 |
| Tocopheryl acetate | 1.00 |
| NaOH | q.s. |
| Perfume, preservative | q.s. |
| Water | ad 100.00 |

EXAMPLE 5

|  | % by weight |
|---|---|
| Glyceryl stearate | 2.00 |
| Methyl glucose sesquistearate | 5.00 |
| Caprylic/capric triglyceride | 1.67 |
| Octyldodecanol | 1.67 |
| $C_{12-15}$-alkyl benzoates | 1.67 |
| Phenylbenzimidazolesulphonic acid | 2.00 |
| Tris-[anilino-(p-carbo-2'-ethyl-1'-hexyloxy)] triazine | 3.00 |
| 4-(Tert-butyl)-4'-methoxydibenzoylmethane | 2.00 |
| Butylene glycol | 3.00 |
| 4-Methylbenzylidenecamphor | 2.00 |
| Tocopheryl acetate | 1.00 |
| NaOH | q.s. |
| Perfume, preservative | q.s. |
| Water | ad 100.00 |

We claim:
1. Cosmetic or dermatological compositions comprising
   (a) one or more surface-active glucose derivatives of the formula

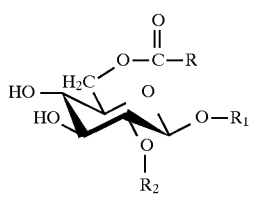

in which R is a branched or unbranched alkyl radical having 1 to 24 carbon atoms, $R_1$ is either a hydrogen atom or a branched or unbranched alkyl radical having 1 to 24 carbon atoms and $R_2$ is either a hydrogen atom or a branched or unbranched acyl radical having 1 to 24 carbon atoms,
   (b) one or more surface-active glycerol monocarboxylic or dicarboxylic acid monoesters of the formula

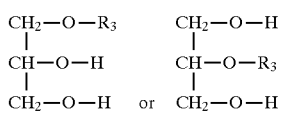

in which $R_3$ is a branched or unbranched acyl radical having 6–24 carbon atoms, and
   (c) one or more water-soluble, cosmetically or pharmaceutically acceptable UV filters.
2. A method of protecting skin from the effects of damaging UV light comprising applying to the skin a protective amount of a cosmetic or dermatological formulation comprising
   (a) one or more surface-active glucose derivatives of the formula

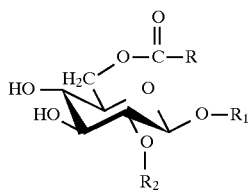

in which R is a branched or unbranched alkyl radical having 1 to 24 carbon atoms, $R_1$ is either a hydrogen atom or a branched or unbranched alkyl radical having 1 to 24 carbon atoms and $R_2$ is either a hydrogen atom or a branched or unbranched acyl radical having 1 to 24 carbon atoms,
   (b) one or more surface-active glycerol monocarboxylic or dicarboxylic acid monoesters of the formula

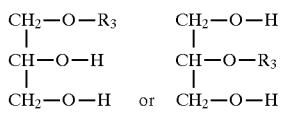

in which $R_3$ is a branched or unbranched acyl radical having 6–24 carbon atoms, and
   (c) one or more water-soluble, cosmetically or pharmaceutically acceptable UV filters, said formulation being optionally in the form of a foam.
3. A method according to claim 2, wherein the formulation is in the form of a foam and the formulation comprises an aqueous phase which optionally comprises conventional substances soluble and/or dispersible therein, and optionally an oil phase which optionally comprises conventional substances soluble or dispersible therein.
4. A method according to claim 2, wherein the water-soluble, cosmetically or pharmaceutically acceptable UV filter or filters comprise UV filters which carry one or more sulphonic acid groups or sulphonate groups on their molecular backbone.
5. A method according to claim 2, wherein the water soluble, cosmetically or pharmaceutically acceptable UV filter or filters are selected from the group consisting of 2-phenylbenzimidazole-5-sulphonic acid and its salts, sulphonic acid derivatives of benzophenones, sulphonic acid derivatives of 3-benzylidene-camphor, 2-methyl-5-(2-oxo-3-bornylidenemethyl)benzenesulphonic acid and its salts, and 1,4-di(2-oxo-10-sulpho-3-bornylidenemethyl)benzene and its salts.
6. A method according to claim 2, wherein the water-soluble UV filter or filters comprise 2-hydroxy4-methoxybenzophenone-5-sulphonic acid or a salt thereof, 4-2-oxo-3-bornylidenemethyl)benzene or its sodium, potassium or triethanolammonium salt, or 2-methyl-5-(2-oxo-3-bornylidenemethyl)benzene-sulphonic acid or its sodium, potassium or triethanolammonium salt.
7. A method according to claim 3, wherein the optional conventional substances which are soluble or dispersible in the aqueous phase or the oil phase optionally comprising cosmetically or pharmaceutically acceptable UV filters other than those previously recited in (c).
8. A method according to claim 2, wherein, in the formula of the surface-active glucose derivatives, the radical R represents myristyl, palmityl, stearyl or eicosyl, the radical $R_1$ represents hydrogen, methyl, ethyl, propyl, or isopropyl, and/or the radical $R_2$ represents hydrogen, myristoyl, palmitoyl, stearoyl or eicosoyl.
9. A method according to claim 2, wherein the surface-active glucose derivative is methyl glucose sesquistearate.
10. A method according to claim 2, wherein the surface-active glycerol monoester is glyceryl stearate.
11. A cosmetic or dermatological formulation for protecting skin from the effects of damaging UV light comprising a skin protective amount of a composition comprising
   (a) one or more surface-active glucose derivatives of the formula

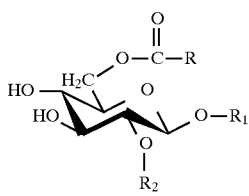

in which R is a branched or uubranched alkyl radical having 1 to 24 carbon atoms, $R_1$ is either a hydrogen atom or a branched or unbranched alkyl radical having 1 to 24 carbon atoms and $R_2$ is either a hydrogen atom or a branched or unbranched acyl radical having 1 to 24 carbon atoms,
   (b) one or more surface-active glycerol monocarboxylic or dicarboxylic acid monoesters of the formula

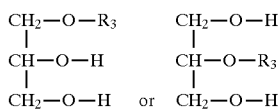

in which R₃ is a branched or unbranched acyl radical having 6–24 carbon atoms, and (c) one or more water-soluble, cosmetically or pharmaceutically acceptable UV filters, said formulation being optionally in the form of a foam.

12. A formulation according to claim 11, wherein the formulation is in the form of a foam and which further comprises an aqueous phase which optionally comprises conventional substances which are soluble and/or dispersible therein, and optionally an oil phase which optionally comprises conventional substances soluble and/or dispersible therein.

13. A formulation according to claim 12, wherein the optional conventional substances which are soluble or dispersible in the aqueous phase or the oil phase optionally comprise cosmetically or pharmaceutically acceptable UV filters other than those previously recited in (c).

14. A formulation according to claim 11, wherein, in the formula of the surface-active glucose derivatives, the radical R represents myristyl, palmityl, stearyl or eicosyl, the radical $R_1$ represents hydrogen, methyl, ethyl, propyl, or isopropyl, and/or the radical $R_2$ represents hydrogen, myristoyl, palmitoyl, stearoyl or eicosoyl.

15. A formulation according to claim 11, wherein the surface-active glucose derivative is methyl glucose sesquistearate.

16. A formulation according to claim 11, wherein the surface-active glycerol monoester is glyceryl stearate.

17. A formulation according to claim 11, wherein the water-soluble, cosmetically or pharmaceutically acceptable UV filter or filters comprise UV filters which carry one or more sulphonic acid groups or sulphonate groups on their molecular backbone.

18. A formulation according to claim 11, wherein the water-soluble, cosmetically or pharmaceutically acceptable UV filter or filters are selected from the group consisting of 2-phenylbenzimidazole-5-sulphonic acid and its salts, sulphonic acid derivatives of benzophenones, sulphonic acid derivatives of 3-benzylidene-camphor, 2-methyl-5-(2-oxo-3-bornylidenemethyl)benzenesulphonic acid and its salts, and 1,4-di(2-oxo-10-sulpho-3-bornylidenemethyl)benzene and its salts.

19. A formulation according to claim 11, wherein the water-soluble UV filter or filters comprise 2-hydroxy-4-methoxybenzophenone-5-sulphonic acid or a salt thereof, 4-2-oxo-3-bornylidenemethyl)benzene or its sodium, potassium or triethanolammonium salt, or 2-methyl-5-(2-oxo-3-bornylidenemethyl)benzene-sulphonic acid or its sodium, potassium or triethanolammonium salt.

* * * * *

UNITED STATES PATENT AND TRADEMARK OFFICE
CERTIFICATE OF CORRECTION

PATENT NO : 5,833,960
DATED : November 10, 1998
INVENTOR(S): Gers-Barlag, et al.

It is certified that error appears in the above-identified patent and that said Letters Patent is hereby corrected as shown below:

Col. 18, claim 6 lines 2-3    Delete " 2-hydroxy4-methoxybenzophenone- " and substitute -- 2-hydroxy-4-methoxy-benzophenone- --

Col. 18, line 60    Delete " uubranched " and substitute -- unbranched --

Signed and Sealed this

Fifteenth Day of February, 2000

Q. TODD DICKINSON

Attest:

Attesting Officer

Commissioner of Patents and Trademarks